United States Patent [19]

Johnson, Jr. et al.

[11] 4,212,297
[45] Jul. 15, 1980

[54] MICRO-FLUID EXCHANGE COUPLING APPARATUS

[76] Inventors: Robert A. Frosch, Administrator of the National Aeronautics and Space Administration, with respect to an invention of John E. Johnson, Jr., Baltimore, Md.; Paul F. Swartz, San Carlos, Calif.

[21] Appl. No.: 951,422

[22] Filed: Oct. 16, 1978

[51] Int. Cl.³ ............................................ A61M 16/00
[52] U.S. Cl. ...................... 128/207.14; 128/204.18; 128/207.28; 128/DIG. 26; 128/236; 128/DIG. 6; 128/DIG. 9; 128/DIG. 12; 128/DIG. 16
[58] Field of Search .................. 128/DIG. 6, DIG. 9, 128/DIG. 26, 351, 134, 145.5, 145.6, 145.8, 184, 208, 213, 222, 223, 247, 218 N, 214 R, 218 A, 240, 305.3, 218 R, 215, 276, 236, DIG. 12, DIG. 16, 204.18, 207.28

[56] References Cited

U.S. PATENT DOCUMENTS

| | | | |
|---|---|---|---|
| 1,793,068 | 2/1931 | Dickinson | 128/218 N |
| 2,266,231 | 12/1941 | Mazzeo et al. | 128/DIG. 26 |
| 3,915,165 | 10/1975 | Rambosek | 128/266 |
| 3,964,481 | 6/1976 | Gourland et al. | 128/218 A |
| 4,108,176 | 8/1978 | Walden | 128/218 A |

Primary Examiner—Henry J. Recla
Attorney, Agent, or Firm—Darrell G. Brekke; John R. Manning; Armand McMillan

[57] ABSTRACT

In a micro-fluid exchange apparatus for exchanging fluid with an organ, such as the trachea or a blood vessel of a small animal, such as a rat or a mouse, a hollow needle, such as a syringe needle, is provided for penetrating the fluid conduit of the animal. The syringe needle is coupled to a plenum chamber having an inlet and outlet port. The plenum chamber is coupled to the syringe needle via the intermediary of a standard quick disconnect coupling fitting. The plenum chamber is carried at the end of a drive rod which is coupled to a micrometer drive head. The micrometer drive head is slidably and pivotably coupled to a pedestal for adjusting the height and angle of inclination of the needle relative to a reference base support. The needle is positioned adjacent to the incised trachea or a blood vessel of a small animal and the micrometer drive head is operated for penetrating the fluid conduit of the animal. In the case of a micro-respirator, an oxygen respirator pump is coupled in gaseous communication with the input and output ports of the plenum chamber for supplying oxygen and withdrawing exhaled gas from the small animal.

1 Claim, 5 Drawing Figures

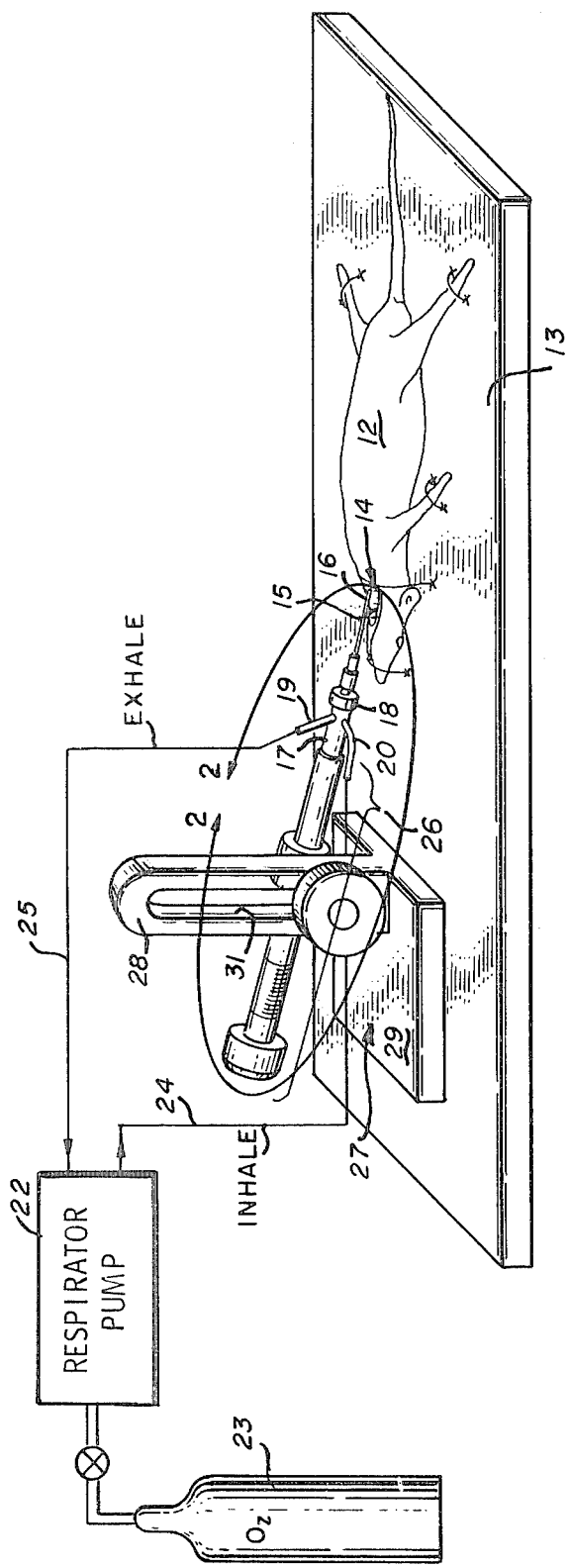

MICRO-FLUID EXCHANGE COUPLING APPARATUS

BACKGROUND OF THE INVENTION (1) Field of the Invention

The present invention relates in general to microfluid exchange apparatus, such as a micro-respirator, for coupling equipment into fluid communication with a fluid conduit, such as the trachea or a blood vessel of a small animal, such as a rat or mouse.

(2) Description of the Prior Art

Heretofore, human tracheostomy devices have been provided for coupling a respirator in fluid communication with the trachea of a human. Such a device consists of a tube which is fed through an incision in the trachea. The tube is coupled to a "T" connector. One arm of the "T" is connected to a source of oxygen to be fed into the lungs of the human, whereas the other arm of the "T" connector is coupled to a pump for pumping the exhaled breath from the patient. Such a device is disclosed in U.S. Pat. No. 2,584,450 issued Feb. 5, 1952.

It is also known from the prior art to provide a micro-injection unit in which a 2 cc syringe is held in a mounting bracket and driven by a 25 mm micrometer head. The mounting bracket and micrometer head are mounted to a base plate. This micro-injection unit has also been adapted for use in stereotaxic instruments in which a piece of needle stock is held in an electrode holder to which is attached a flexible tube. The flexible tube in turn is attached to the needle held on the syringe which is driven by the micrometer head. Such a micro-injection unit is commercially available as model 1208, from David Kopf Instruments of Tujunga, Calif.

There has developed a need for a micro-respirator or microperfusion device which will allow surgery to be performed on small animals, such as rats, mice, etc., by one experimenter. More particularly, it is desired to provide a micro-respirator, whereby a blunt needle (Cannula) head is held steadfastly in place without causing pressure on structures below or to the side of the trachea while performing thoracic surgery on small animals such as rats or mice by one experimenter.

SUMMARY OF THE PRESENT INVENTION

The principal object of the present invention is the provision of an improved micro-fluid exchange coupling apparatus for exchanging gas or liquid with the organs of small animals, such as rats or mice.

In one feature of the present invention, a plenum chamber having inlet and outlet ports is coupled in fluid communication with a hollow needle for penetrating a vessel of a small animal and the plenum chamber is coupled to a micrometer head for translation of the needle into the vessel.

In another feature of the present invention, the micrometer head, plenum chamber and needle are pivotably coupled to a pedestal for selecting the angle of inclination of the needle relative to a base support, which is to support the animal during the procedure.

In another feature of the present invention, an oxygen respirator pump is coupled to the input and output ports of the plenum chamber to control the air pressure and inhale and exhale periods for the small animal during a surgery procedure.

Other features and advantages of the present invention will become apparent upon a perusal of the following specification taken in connection with the accompanying drawings wherein:

BRIEF DESCRIPTION OF THE DRAWINGS

FIG. 1 is a perspective schematic drawing, partly in block diagram form, depicting a micro-respirator system incorporating features of the present invention, FIG. 2 is an enlarged schematic view of a portion of the structure of FIG. 1 delineated by line 2—2, FIGS. 3 (a-f) is a composite piece part drawing for the micrometer driven syringe structure of FIG. 2 and incorporating features of the present invention.

DESCRIPTION OF THE PREFERRED EMBODIMENTS

Figure 3:
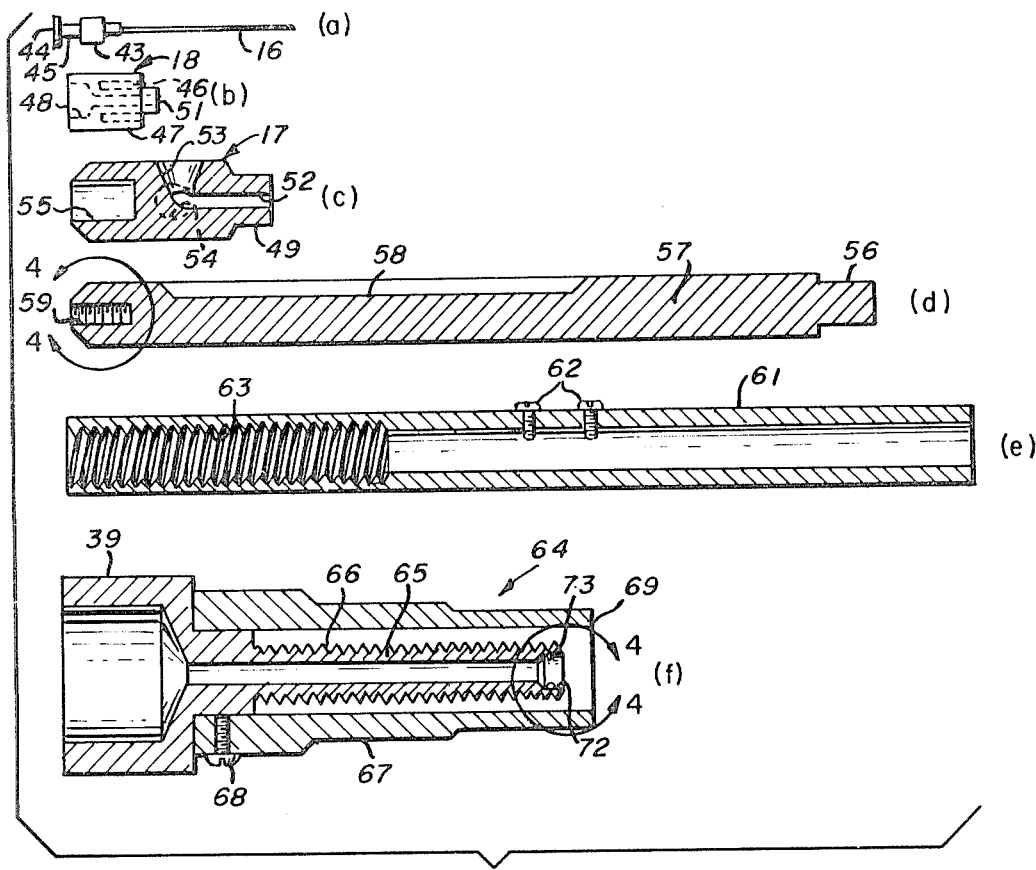

Referring now to FIGS. 1–5 there is shown a micro-respirator system 11, incorporating features of the present invention, for respirating a small animal, such as a mouse or a rat 12 during a surgical procedure to be performed on the mouse or rat 12 by a single experimenter.

The rat or mouse 12 is anesthetized and strapped down to a reference base support 13 in a spread eagle fashion as shown in FIG. 1. An incision 14 is made in the neck of the animal 12 over the trachea 15 and the skin and muscles are separated and tied to the reference support 13 for exposing the trachea 15. A small hole is made in the trachea to receive the tip of a syringe needle 16.

The syringe needle 16 is connected in fluid communication with a plenum chamber 17 via the intermediary of a standard quick disconnect syringe fitting 18. A pair of tubes 19 and 20 are coupled in fluid communication with the plenum chamber 17. The tubes 19 and 20 are orthogonally displaced peripherally with respect to each other so as to facilitate coupling of tubes to the tubes 19 and 20. A respirator pump 22 is provided to control the air pressure and the inhale-exhale periods or respiration. Oxygen mixtures are supplied to the pump 22 from a compressed air tank 23. The inhale valve portion, not shown, of the respirator pump 22 is connected to inhale tube 20 of the plenum chamber 17 by means of tubing 24 and the exhale valve, not shown, of the respirator pump 22 is connected to the exhale tube 19 of the plenum chamber 17 via tubulation 25.

A micrometer head 26 is coupled to the plenum chamber 17 for imparting axial translation to the plenum chamber 17 and thence to the syringe needle 16 for advancing the needle 16 through the hole into the trachea 15 for providing fluid communication between the respirator pump 22 and the trachea of the animal 12. The micrometer head 26 is pivotably coupled to a pedestal 27 which is supported from the reference base support 13.

The pedestal 27 includes an upstanding elongated plate 28 mounted to a plate-like foot portion 29. The upstanding portion 28 includes a vertical slot 31 to receive a stud 32 which is horizontally directed through and which slides vertically in the slot 31. The stud 32 is fixedly coupled to a cylindrical holder 33 having a transverse bore 34 extending therethrough. A Telfon sleeve 35 is mounted within the bore 34 and surrounds the micrometer head 26 slideably received within the sleeve 35. A nylon cylindrical sleeve 36 receives the cylindrical holder 33 therewithin and a knurled nut 37 is threadably mated with the stud 32. A Telfon washer 38 is disposed in between the nut 37 and the vertical plate 28.

The vertical position of the micrometer head 26 is determined by loosening the nut 37 and adjusting the height of the stud 32 with respect to the foot 29 and reference base support 13. The angle of inclination between the micrometer head 26 and the reference base support 13 is selected by loosening the knurled nut 37 and adjusting the angle of inclination of the micrometer head 26. After the adjustment is made, the knurled nut 37 is tightened, thereby frictionally locking the micrometer head 26 to the plate 28 via the frictional engagement between the outer end of the cylindrical sleeve 36 and the inner side edge of the micrometer head 26.

Once the angle of inclination is established, the knurled end 39 of the micrometer head 26 is rotated in the clockwise direction so as to advance the plenum chamber 17 with attached syringe needle 16 into and through the opening in the trachea 15 so as to place the respirator pump 22 in gas communication with the trachea for respirating the animal 12. The thorax of the small animal can then be opened and surgery performed by a single experimenter.

The quick disconnect coupling 18 is designed to fit standard syringe needles of any size for the small tracheas of mice as well as the larger tracheas of rats. The micrometer scale 42 is observed while translating the syringe needle 16 into the trachea 15 a predetermined distance (2-4 mm for a mouse). The fluid exchange apparatus of the present invention is also particularly useful for perfusing rats and mice with fixative for electron microscopy.

Referring now to FIG. 3, the piece parts of the micrometer head 26, plenum chamber 17, quick disconnect fitting 18, and syringe needle 16 are shown in greater detail. More particularly, in FIG. 3 (a) the standard syringe needle 16 is depicted. The syringe needle includes a square collar portion 43 to be grasped by the fingers of the operator for threadably inserting the syringe needle into the quick disconnect coupling 18. The fingers grasp the rectangular collar 43 for turning the needle 16 for threadably mating a rectangular flange 44 at the end of a tubular segment 45 with internal threads 46 of the quick disconnect coupling 18, shown in FIG. 3 (b).

The quick disconnect coupling 18 includes a hollow cylindrical housing 47 with a re-entrant bore 48 at one end to receive the male portion 49 of the plenum chamber 17 as shown in FIG. 3 (c). A male tubular portion 51 of the quick disconnect 18 is received within the tubular segment 45 of the syringe needle 16. An annular re-entrant bore, which is internally threaded at 46, surrounds tube 51 and receives the flanged end 44 of the syringe needle 16.

The plenum chamber 17 (see FIG. 3 (c)) inlcudes an axially directed bore 52 which is coupled in fluid communication with the axial bore through the quick disconnect coupling 18. A pair of radial bores 53 and 54 intersect the longitudinal bore 52 at 90 degree intervals about the periphery of the plenum chamber 17. The bores 53 and 54 receive the ends of tubes 19 and 20. A re-entrant bore 55 in the plenum member 17 receives the male end 56 of a cylindrical drive rod 57 (see FIG. 3 (d)).

The drive rod includes a longitudinally directed key slot 58. A re-entrant threaded bore 59 is provided at the other end of the drive rod 57. The drive rod is received axially within a sleeve 61 (see FIG. 3 (e)) having a pair of adjustable set screws 62 extending radially inwardly of the sleeve 61 for sliding within the key slot 58. The set screws 62 are disposed in axial alignment with the longitudinal axis of the sleeve 61 and serve to prevent rotation of the drive rod 57 within the sleeve 61 while permitting axial translation of the drive rod 57 within the sleeve 61. Internal acme threads 63 are provided at one end of the sleeve 61 for threadably mating with externally threads of a drive nut 64 of FIG. 3 (f).

The drive nut 64 includes the knurled knob portion 39 with an axially directed tubular extension 65 provided with external acme threads 66 for threadably mating with the internal threads 63 of the sleeve 61. A cylindrical collar 67 is affixed to the knob 39 via set screw for rotation and axial translation therewith.

The collar 67 also serves as a dust shield to protect the threads 66. The inner end 69 of the outer collar 67 serves, in cooperation with the scale 42, to determine the axial position of the syringe 61. A re-entrant bore 72 is provided at the inner end of the inside tubular portion 65 of the drive nut 64. A retaining ring 73 is carried at the inner lip of the re-entrant bore 72.

Figure 4:
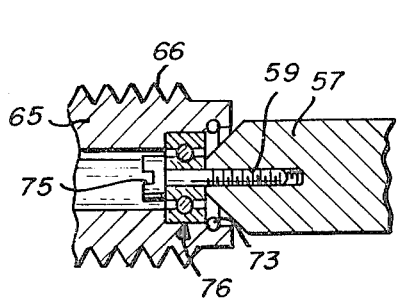
FIG. 4 is an enlarged sectional view of a portion of the structure of FIGs. 3 (d) and (f) delineated by line 4—4 and, FIG. 5 is an enlarged sectional view of a portion of the structure of FIG. 2 taken along line 5—5 in the direction of the arrows.
Figure 5:
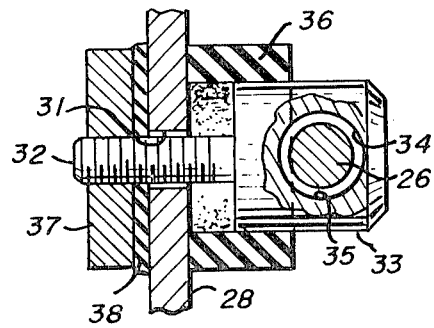

Referring now to FIG. 4, the coupling of the drive nut 64 to the drive rod 57 is shown in greater detail. A cap screw 75 is threaded into the internal bore 59 of the drive rod 57 and the shank of the cap screw 75 is circled by a thrust ball bearing assembly 76. The outer race of the ball bearing assembly 76 is captured by the retaining ring 73 against relative axial translation between the drive nut 64 and the outer race for transmitting axial thrust to the drive rod 57 while permitting relative rotation between the drive nut 64 and the drive rod 57.

Thus, in operation, rotation of the drive nut via knurled knob 39 causes the drive nut 64 to travel within the sleeve 61 and to transmit axial translation to the drive rod 57. The drive rod 57 is held against rotation by means of the set screws 62 riding in the key slot 58. The amount of axial translation of the drive and thus of the plenum 17 and the syringe 16 is monitored by observing the position of the inner end 69 of the drive nut 64 relative to the scale 42 provided on the outer surface of the sleeve 61.

What is claimed is:

1. In a micro-fluid exchange apparatus for exchanging fluid within an organ of a small animal such as a rat or mouse via the intermediary of a hollow needle for penetrating a fluid conduit of the small animal for connecting the hollow needle in fluid exchanging relation with the fluid conduit such as a trachea or blood vessel of the small animal;

plenum means comprising a chamber having inlet and outlet port means for connection in fluid communication with the hollow needle for passage of fluid therethrough into and out of the fluid conduit of the small animal via the intermediary of the hollow needle;

pedestal means for pivotably holding the hollow needle at any one of a selected number of angles of inclination relative to a reference base support to which the small animal is to be held during the procedure;

translating means for translating the hollow needle into the fluid conduit of the small animal or along the longitudinal axis of the elongated hollow needle;

said translating means including an elongated hollow sleeve adapted to be secured to said pedestal means, a drive rod axially translatable within said sleeve means, key means for keying said drive rod means to said sleeve means to allow axial translation therewithin without substantial rotation therebetween;

means for coupling the hollow needle and said plenum means to said drive rod for axial translation therewith;

said sleeve means including a threaded portion;

rotatable drive means having a threaded portion for mating with said threaded portion of said sleeve means for axial translation within said sleeve means for effecting relative rotation between said sleeve means and said rotatable drive means;

means for coupling said rotatable drive means to said drive rod; and readout means coupled to said drive rod for axial translation therewith for reading out the axial position of said drive rod relative to said sleeve means.

* * * * *